United States Patent
Guevremont et al.

(10) Patent No.: US 7,812,309 B2
(45) Date of Patent: Oct. 12, 2010

(54) APPARATUS AND METHOD FOR AN ELECTRO-ACOUSTIC ION TRANSMITTOR

(75) Inventors: Roger Guevremont, Ottawa (CA); Govindanunny Thekkadath, Ottawa (CA); Maria Guevremont, Ottawa (CA)

(73) Assignee: Thermo Finnigan LLC, San Jose, CA (US)

(*) Notice: Subject to any disclaimer, the term of this patent is extended or adjusted under 35 U.S.C. 154(b) by 438 days.

(21) Appl. No.: 11/815,761

(22) PCT Filed: Feb. 9, 2006

(86) PCT No.: PCT/CA2006/000181

§ 371 (c)(1),
(2), (4) Date: May 19, 2008

(87) PCT Pub. No.: WO2006/084363

PCT Pub. Date: Aug. 17, 2006

(65) Prior Publication Data

US 2009/0127457 A1    May 21, 2009

Related U.S. Application Data

(60) Provisional application No. 60/650,970, filed on Feb. 9, 2005.

(51) Int. Cl.
*H01J 49/22* (2006.01)
*H01J 49/06* (2006.01)

(52) U.S. Cl. ............... 250/290; 250/281; 250/282; 250/292

(58) Field of Classification Search .......... 250/281, 250/282, 283, 290, 291, 292, 294, 295, 296, 250/297
See application file for complete search history.

(56) References Cited

U.S. PATENT DOCUMENTS

| | | | |
|---|---|---|---|
| 3,621,240 A * | 11/1971 | Cohen et al. ............ 250/282 |
| 4,066,893 A | 1/1978 | Dawson |
| 6,216,538 B1 | 4/2001 | Yasuda et al. |
| 6,566,652 B1 * | 5/2003 | Kato ................... 250/288 |
| 6,653,627 B2 | 11/2003 | Guevremont et al. |
| 6,799,355 B2 | 10/2004 | Guevremont et al. |
| 2003/0020012 A1 * | 1/2003 | Guevremont ........... 250/287 |
| 2003/0213904 A9 * | 11/2003 | Guevremont et al. ...... 250/287 |
| 2004/0041090 A1 * | 3/2004 | Bloomfield et al. ...... 250/282 |
| 2008/0191130 A1 * | 8/2008 | Bateman et al. ........ 250/283 |

* cited by examiner

*Primary Examiner*—Jack I Berman
*Assistant Examiner*—Nicole Ippolito Rausch
(74) *Attorney, Agent, or Firm*—Charles B. Katz

(57) ABSTRACT

A method of transmitting ions along an analyzer region between closely spaced electrodes is disclosed. The method includes providing an analyzer region for transmitting ions, the analyzer region in fluid communication with an ionization source and with an ion detecting device. The method further includes affecting a pressure within at least one portion of the analyzer region, to differ from the pressure within another part of the analyzer region, and providing an electric field that is synchronized with the pressure differences to focus the ions.

21 Claims, 12 Drawing Sheets

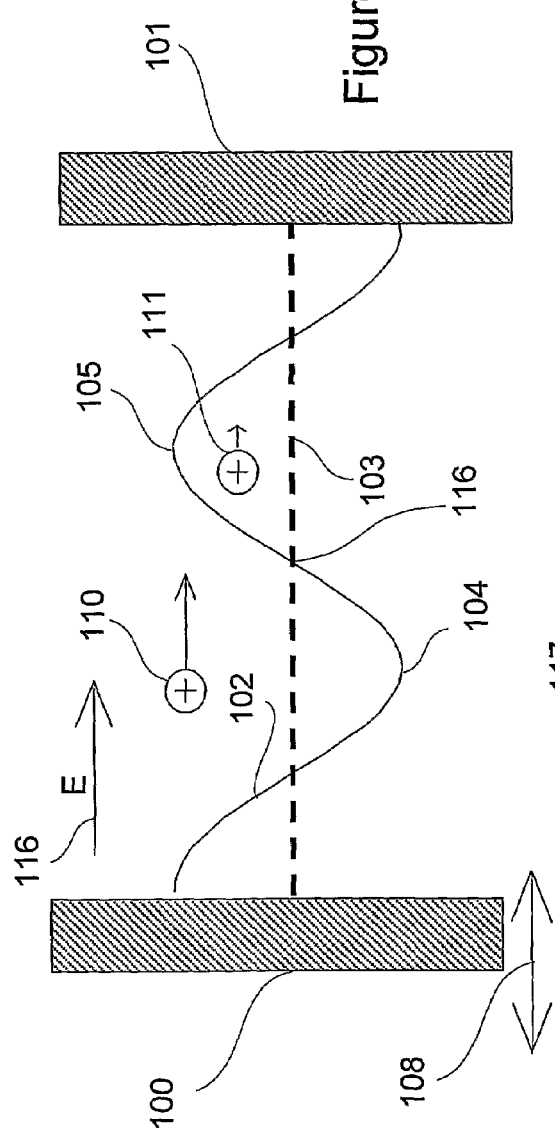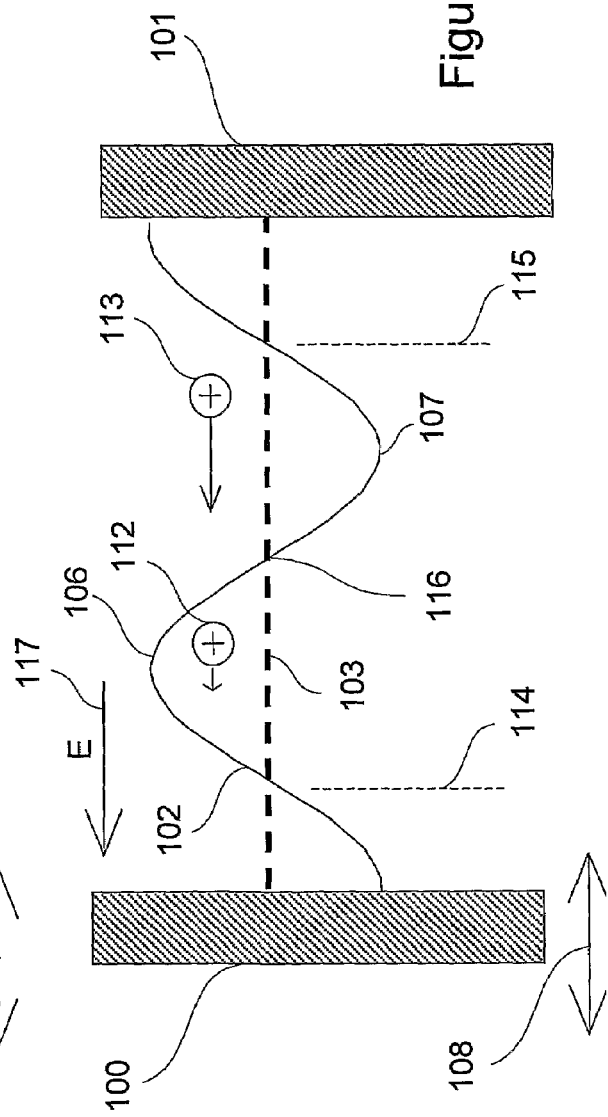

APPARATUS AND METHOD FOR AN ELECTRO-ACOUSTIC ION TRANSMITTOR

CROSS-REFERENCE TO RELATED APPLICATIONS

This application is a National Stage application under 35 U.S.C. §371 of PCT Application No. PCT/CA2006/000181, filed Feb. 9, 2006, entitled "Apparatus and Method for an Electro-Acoustic Ion Transmittor", which claims the priority benefit of U.S. Provisional Patent Application No. 60/650, 970, filed Feb. 9, 2005, entitled "Apparatus and Method for an Electro-Acoustic Ion Transmittor", which applications are incorporated herein by reference in their entireties.

This application claims benefit from U.S. Provisional application 60/650,970 filed Feb. 9, 2005, the entire contents of which are incorporated herein by reference.

FIELD OF THE INVENTION

The instant invention relates generally to ion transmission between closely spaced electrodes. In particular, the instant invention relates to methods and apparatus for providing acoustic pressure waves and electric fields within a carrier gas between the electrodes to form a novel ion transmission region.

BACKGROUND OF THE INVENTION

High sensitivity and amenability to miniaturization for field-portable applications have helped to make ion mobility spectrometry (IMS) an important technique for the detection of many compounds, including narcotics, explosives, and chemical warfare agents as described, for example, by G. Eiceman and Z. Karpas in their book entitled "Ion Mobility Spectrometry" (CRC, Boca Raton, 1994). In IMS, gas-phase ion mobilities are determined using a drift tube with a constant electric field. Ions are separated in the drift tube on the basis of differences in their drift velocities. At low electric field strength, for example 200 V/cm, the drift velocity of an ion is proportional to the applied electric field strength, and the mobility, K, which is determined from experimentation, is independent of the applied electric field. Additionally, in IMS the ions travel through a bath gas that is at sufficiently high pressure that the ions rapidly reach constant velocity when driven by the force of an electric field that is constant both in time and location. This is to be clearly distinguished from those techniques, most of which are related to mass spectrometry, in which the gas pressure is sufficiently low that, if under the influence of a constant electric field, the ions continue to accelerate.

E. A. Mason and E. W. McDaniel in their book entitled "Transport Properties of Ions in Gases" (Wiley, New York, 1988) teach that at high electric field strength, for instance fields stronger than approximately 5,000 V/cm, the ion drift velocity is no longer directly proportional to the applied electric field, and K is better represented by $K_H$, a non-constant high field mobility term. The dependence of $K_H$ on the applied electric field has been the basis for the development of high field asymmetric waveform ion mobility spectrometry (FAIMS). Ions are separated in FAIMS on the basis of a difference in the mobility of an ion at high field strength, $K_H$, relative to the mobility of the ion at low field strength, K. In other words, the ions are separated due to the compound dependent behavior of $K_H$ as a function of the applied electric field strength.

In general, a device for separating ions according to the FAIMS principle has an analyzer region that is defined by a space between first and second spaced-apart electrodes. The first electrode is maintained at a selected dc voltage, often at ground potential, while the second electrode has an asymmetric waveform V(t) applied to it. The asymmetric waveform V(t) is composed of a repeating pattern including a high voltage component, $V_H$, lasting for a short period of time $t_H$ and a lower voltage component, $V_L$, of opposite polarity, lasting a longer period of time $t_L$. The waveform is synthesized such that the integrated voltage-time product, and thus the field-time product, applied to the second electrode during each complete cycle of the waveform is zero, for instance $V_H t_H + V_L t_L = 0$; for example +2000 V for 10 µs followed by −1000 V for 20 µs. The peak voltage during the shorter, high voltage portion of the waveform is called the "dispersion voltage" or DV, which is identically referred to as the applied asymmetric waveform voltage.

Generally, the ions that are to be separated are entrained in a stream of gas flowing through the FAIMS analyzer region, for example between a pair of horizontally oriented, spaced-apart electrodes. Accordingly, the net motion of an ion within the analyzer region is the sum of a horizontal x-axis component due to the stream of gas and a transverse y-axis component due to the applied electric field. During the high voltage portion of the waveform, an ion moves with a y-axis velocity component given by $v_H = K_H E_H$, where $E_H$ is the applied field, and $K_H$ is the high field ion mobility under operating electric field, pressure and temperature conditions. The distance traveled by the ion during the high voltage portion of the waveform is given by $d_H = v_H t_H = K_H E_H t_H$, where $t_H$ is the time period of the applied high voltage. During the longer duration, opposite polarity, low voltage portion of the asymmetric waveform, the y-axis velocity component of the ion is $v_L = K E_L$, where K is the low field ion mobility under operating pressure and temperature conditions. The distance traveled is $d_L = v_L t_L = K E_L t_L$. Since the asymmetric waveform ensures that $(V_H t_H) + (V_L t_L) = 0$, the field-time products $E_H t_H$ and $E_L t_L$ are equal in magnitude. Thus, if $K_H$ and K are identical, $d_H$ and $d_L$ are equal, and the ion is returned to its original position along the y-axis during the negative cycle of the waveform. If at $E_H$ the mobility $K_H > K$, the ion experiences a net displacement from its original position relative to the y-axis. For example, if a positive ion travels farther during the positive portion of the waveform, for instance $d_H > d_L$, then the ion migrates away from the second electrode and eventually is neutralized at the first electrode.

In order to reverse the transverse drift of the positive ion in the above example, a constant negative dc voltage is applied to the second electrode. The difference between the dc voltage that is applied to the first electrode and the dc voltage that is applied to the second electrode is called the "compensation voltage" (CV). The CV prevents the ion from migrating toward either the second or the first electrode. If ions derived from two compounds respond differently to the applied high strength electric fields, the ratio of $K_H$ to K may be different for each compound. Consequently, the magnitude of the CV that is necessary to prevent the drift of the ion toward either electrode is also different for each compound. Thus, when a mixture including several species of ions, each with a unique $K_H/K$ ratio, is being analyzed by FAIMS, only one species of ion is selectively transmitted to a detector for a given combination of CV and DV. In one type of FAIMS experiment, the applied CV is scanned with time, for instance the CV is slowly ramped or optionally the CV is stepped from one voltage to a next voltage, and a resulting intensity of transmitted ions is measured. In this way a CV spectrum showing the total ion current as a function of CV, is obtained.

Numerous ionization sources, including atmospheric pressure ionization sources, have been described for use with FAIMS. In addition, detection of ions using several types of detectors, including mass spectrometry is known.

It would be advantageous to provide a method and apparatus for increasing ion transmission efficiency between closely spaced electrodes. In particular, it would be advantageous to provide a method and apparatus for increasing ion transmission efficiency between closely spaced electrodes of a FAIMS analyzer.

SUMMARY OF THE INVENTION

It is an object of at least one embodiment of the instant invention to modify the separation of ions by influencing the field E/N by application of acoustic pressure waves between the electrodes of FAIMS.

It is an object of at least one embodiment of the instant invention to form standing acoustic pressure waves across the analyzer region of FAIMS, the standing acoustic pressure waves beneficially affecting the separation of ions.

It is an object of at least one embodiment of the instant invention to affect ion transmission and ion separation by forming a pathway between the ion inlet and the ion outlet of a FAIMS analyzer, the pathway comprising standing acoustic waves and synchronized applied electric fields that selectively transmit ions from a mixture provided into the ion inlet of FAIMS.

It is an object of at least one embodiment of the instant invention to transmit ions using acoustic pressure waves, the acoustic waves formed in specific amplitude and phase relationship with an applied sinusoidal voltage difference between a set of electrodes, based on low-field mobility of the ions, to provide an ion focusing mechanism. The ion focusing mechanism being useable independently without FAIMS, or in a tandem arrangement where FAIMS is before the electroacoustic transmission device or FAIMS is after the electroacoustic transmission device.

It is an object of at least one embodiment of the instant invention to operate a device capable of both FAIMS separation mode and an electro-acoustic ion transmission mode alternately in time.

According to an aspect of the instant invention there is provided an apparatus for separating ions, comprising: a first electrode and a second electrode disposed one relative to the other in a spaced-apart facing arrangement for defining an analyzer region therebetween, the analyzer region including an ion origin end and an ion exit end and having a length extending between the ion origin end and the ion exit end; an electrical contact on one of the first electrode and the second electrode for receiving an electrical signal from a power supply for providing a voltage difference across the analyzer region between the first electrode and the second electrode; and, an acoustic pressure wave generator for providing an acoustic pressure wave within the analyzer region between the first electrode and the second electrode.

According to another aspect of the instant invention there is provided a method of separating ions, comprising: providing an analyzer region for separating ions and defined by a space between a first electrode surface and a second electrode surface, the first electrode surface disposed in a spaced-apart facing relationship with the second electrode surface, the analyzer region in fluid communication with an ionization source and with an ion detecting device; providing an electric field within the analyzer region by the application of a potential difference between the first electrode surface and the second electrode surface, the electric field for affecting trajectories of ions along a direction normal to the first electrode surface and the second electrode surface; providing a gas within the analyzer region; and, affecting the pressure of the gas within the analyzer region such that the gas pressure in a first portion of the analyzer region differs from the gas pressure in a second portion of the analyzer region.

According to still another aspect of the instant invention there is provided a method of separating ions, comprising: providing an analyzer region for separating ions and defined by a space between a first electrode and a second electrode, the first electrode comprising a first electrode surface and the second electrode comprising a second electrode surface, the first electrode surface disposed in a spaced-apart facing relationship with the second electrode surface, the analyzer region in fluid communication with an ionization source and with an ion detecting device; providing a mechanical oscillator coupled to one of the first electrode and the second electrode; introducing from the ionization source into the analyzer region a mixture of ions including a predetermined species of ion; providing an electric field within the analyzer region by the application of a potential difference between the first electrode surface and the second electrode surface; driving the mechanical oscillator at a selected frequency for inducing a motion in the one of the first electrode and the second electrode, the selected frequency for supporting formation of an acoustic pressure wave within the analyzer region; and, transmitting the predetermined species of ion through the analyzer region to the ion detecting device

BRIEF DESCRIPTION OF THE DRAWINGS

Exemplary embodiments of the invention will now be described in conjunction with the following drawings, in which similar reference numerals designate similar items:

FIG. 4a is similar to FIG. 3a with the motions of ions shown at points in time when the electric field and the acoustic pressure waves are synchronized;

FIG. 4b is similar to FIG. 3b with the motions of ions shown at points in time when the electric field and the acoustic pressure waves are synchronized;

DESCRIPTION OF EMBODIMENTS OF THE INVENTION

Figure 1:
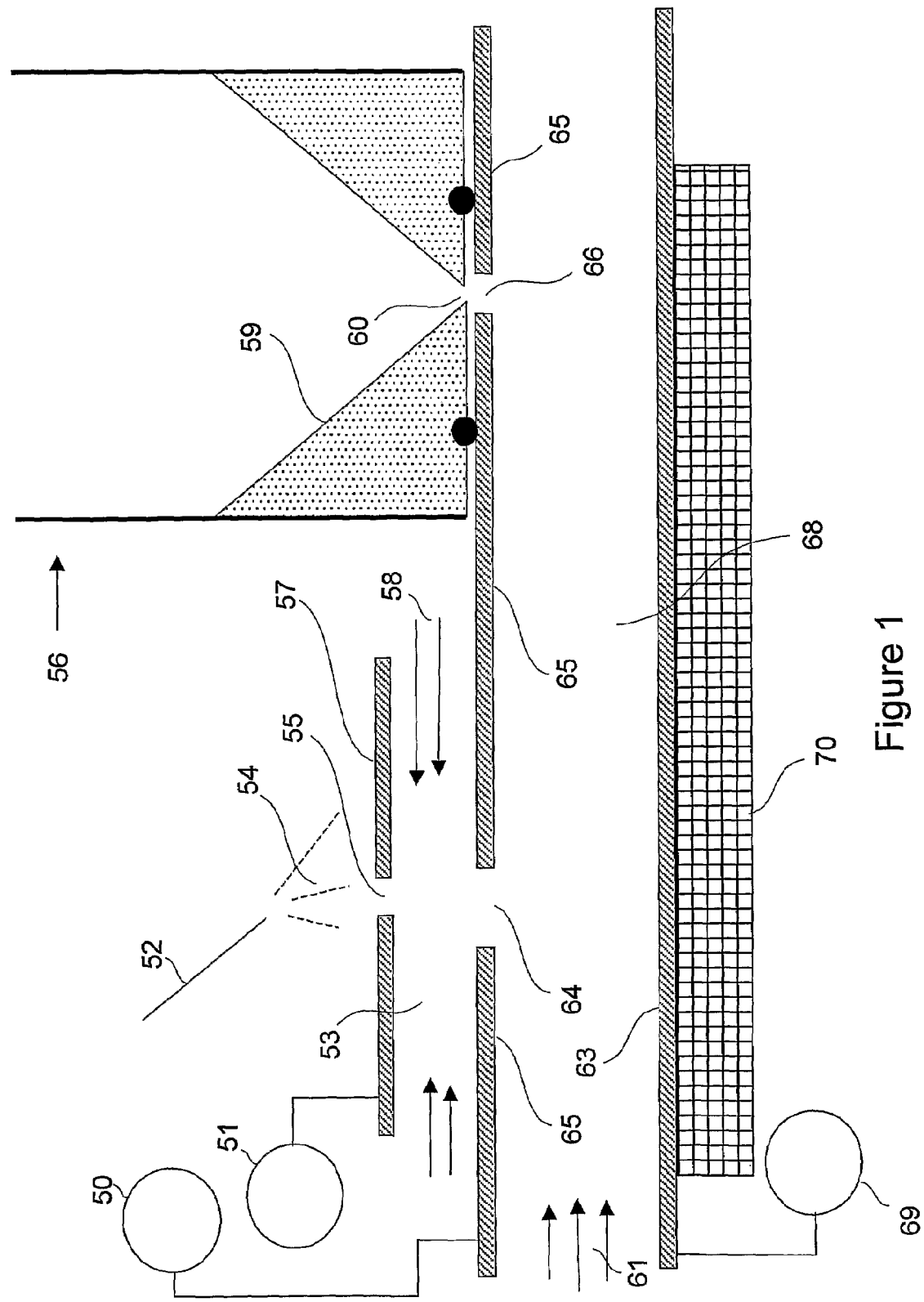
FIG. 1 is a cross section view of parallel plate FAIMS with a piezoelectric element for vibrating one of the electrodes.

The following description is presented to enable a person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and the scope of the invention. Thus, the present invention is not intended to be limited to the embodiments disclosed, but is to be accorded the widest scope consistent with the principles and features disclosed herein.

Throughout much of the following discussion it is assumed that the FAIMS electrodes are operating at atmospheric pressure, but the discussion below is equally applicable at pressures below and at pressures exceeding ambient atmospheric pressure conditions. It is also assumed that the FAIMS electrodes are operated at a selected temperature, which is optionally ambient temperature or a temperature higher than or lower than ambient. Similarly, a newly introduced mechanism called "electro-acoustic ion transmission mode" is operable over a wide range of conditions of pressure and temperature.

In cylindrical and spherical geometry FAIMS it is known that an ion focusing mechanism is a result of the gradient of E/N that forms between the inner and outer electrode. This ion focusing causes the ion cloud to be constrained in the vicinity of an optimal radial location between the electrodes, and therefore assists in minimization of ion loss to the electrode walls. Moreover, a gradient of E/N is established when a gradient of the temperature of the gas between the inner and outer electrode is formed. For example a gradient of E/N is produced when a voltage difference is applied between two electrodes across a region where the gas adjacent to a first electrode is at higher temperature than the gas adjacent to the second electrode, and where the temperature in the gas between the electrodes gradually varies between the two temperatures. In this example the value of N, the number density of the gas, varies with temperature and therefore changes the value of E/N as a function of the temperature. The gradient of E/N induced by temperature gradients in the gas between FAIMS electrodes is used to beneficially modify the focusing properties of both cylindrical and parallel plate versions of FAIMS.

The parallel plate version of FAIMS is known to lack focusing properties away from the edges of the plates, in the absence of temperature gradients between the electrodes, whereas a beneficial focusing effect occurs if temperature conditions between the electrodes serve to mimic the E/N gradient that is found in cylindrical geometry FAIMS. The transmission of ions at a fixed CV requires control of the temperature of the gas and the electrodes, such that the CV conditions for transmission of a selected ion do not change excessively during the time it takes for an ion to pass between the electrodes. It is beneficial that the CV of transmission is constant throughout the device, while simultaneously affecting the temperature of the gas between the electrodes to create conditions for focusing of the ion cloud.

Referring now to FIG. 1, illustrated is a flat plate geometry FAIMS device that is operated in a tandem arrangement with an electrospray ionization source and a mass spectrometer used for ion mass analysis and detection. In this example, ions are formed from a flow of liquid sample in an ionization region 54 adjacent to an electrospray needle 52 held at high potential relative to a curtain plate 57. Some of the ions thus formed pass through the curtain plate aperture 55 against a counter-flow of curtain gas 58 supplied to the region 53 between the curtain plate 57 and the outer FAIMS electrode 65. The region 53 between the curtain plate 57 and the outer FAIMS electrode 65 is enclosed by not-shown insulating material so that the curtain gas 58 is able to exit only through the curtain plate aperture 55 and/or through the ion inlet 64 to the FAIMS analyzer region 68. The portion of curtain gas flow 58 that passes through the ion inlet 64 helps carry ions into an ion origin end of the analyzer region 68, where the flow of gas through ion inlet 64 combines with the flow 61 to transport the ions to the ion outlet 66 at the ion exit end of the analyzer region 68. During transport along the analyzer region 68 between the ion origin end and the ion exit end, the ions are separated according to the FAIMS mechanism. A high voltage rf frequency asymmetric waveform is applied, via a not illustrated electrical contact on electrode 63, to electrode 63 from power supply 69. The voltage on upper plate 65 is provided by power supply 50, via a not illustrated electrical contact on upper plate 65. The voltages and width of the analyzer region 68, as well as other operational variables including gas composition, gas pressure, gas temperature, gradient in temperature of the gas across the analyzer region 68, are selected to support transmission of a subset of the ions provided from the ionization source to the ion outlet 66, and subsequently to an ion detection system 56, which is a mass spectrometer ion inlet system in this non-limiting example. Since the electric field between two flat parallel plates is uniform away from edges, the FAIMS ion focusing mechanism typical of cylindrical geometry electrodes does not function between the flat parallel plates away from edges. Lacking a mechanism for ion focusing, the transmission of an ion between the ion inlet 64 and the ion outlet 66 is inefficient.

Still referring to FIG. 1, in addition to control of the operational variables noted above an acoustic pressure wave generator, such as for instance a mechanical oscillator 70, serves to move the electrode 63 in a rapid oscillation in a direction towards and away from the upper electrode 65. This rapid back-and-forth motion produces a series of acoustic waves that move towards the upper electrode 65. Selection of a frequency of oscillation for the mechanical oscillator 70 forms standing acoustic waves across the analyzer region 68. The stream of ions that is carried from the ion inlet 64 to the ion outlet 66 is selectively located in regions of the acoustic wave, thereby providing a new tool for improving the efficiency of ion transmission. Optionally, both electrodes are equipped with acoustic pressure wave generators. Further optionally, a not-illustrated controller is used to generate oscillations of the two electrodes in a selected amplitude and phase relationship one relative to the other, so as to form a desired acoustic pressure wave, or pattern of waves, in the medium between the electrodes.

Figure 2:
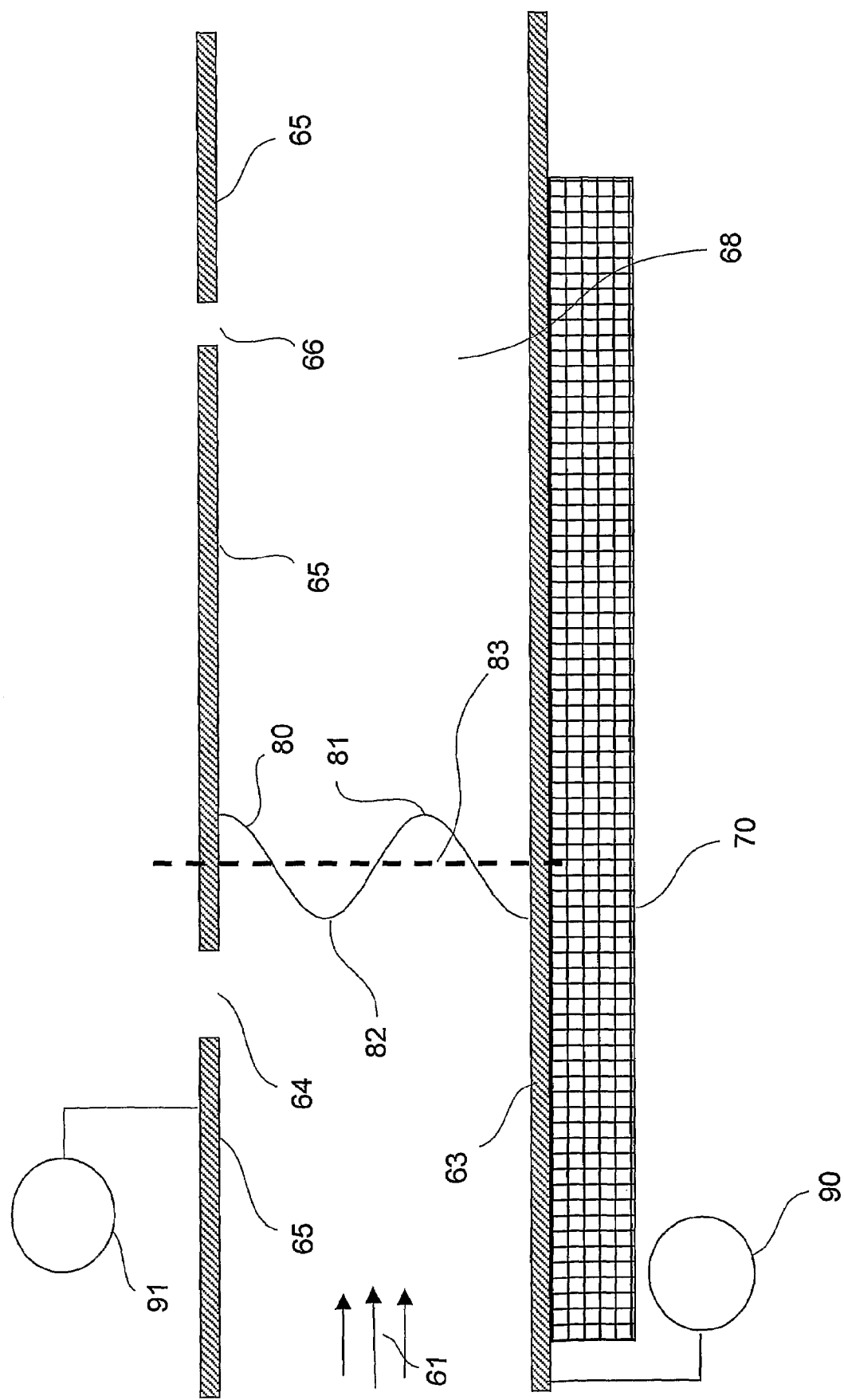
FIG. 2 is an expanded view of the parallel plate FAIMS shown in FIG. 1, illustrating an acoustic standing pressure wave between the electrodes.

FIG. 2 is an expanded view of the parallel electrodes shown in FIG. 1. Items in FIG. 2 with the same reference numerals have the same function as those in FIG. 1. In a non-limiting example, the frequency of the motion produced by mechanical oscillator 70 is selected so that a single standing wave 80 forms across the analyzer region 68. The standing wave 80 is drawn to show a relative high pressure region 81 and a low pressure region 82 at a particular point in time taken with respect to the dashed line 83 which represents the average pressure in the analyzer region 68 absent an acoustic wave or other pressure deviations. A voltage difference is applied across the analyzer region 68 with power supplies 90 and 91. The voltages are optionally a superposition of one or more of an asymmetric waveform typical of FAIMS, a compensation voltage typical of FAIMS and a sinusoidal ripple voltage. As a second, non-limiting example, the asymmetric waveform voltage is removed, and only a compensation voltage and a sinusoidal ripple voltage is applied across the analyzer region 68. As a third, non-limiting example, the asymmetric waveform typical of FAIMS, and the compensation voltage typical of FAIMS are applied. As a fourth, non-limiting example, only a sinusoidal ripple voltage is applied across the analyzer region 68, the ripple voltage optionally synchronized with the acoustic pressure wave.

Figure 3A:
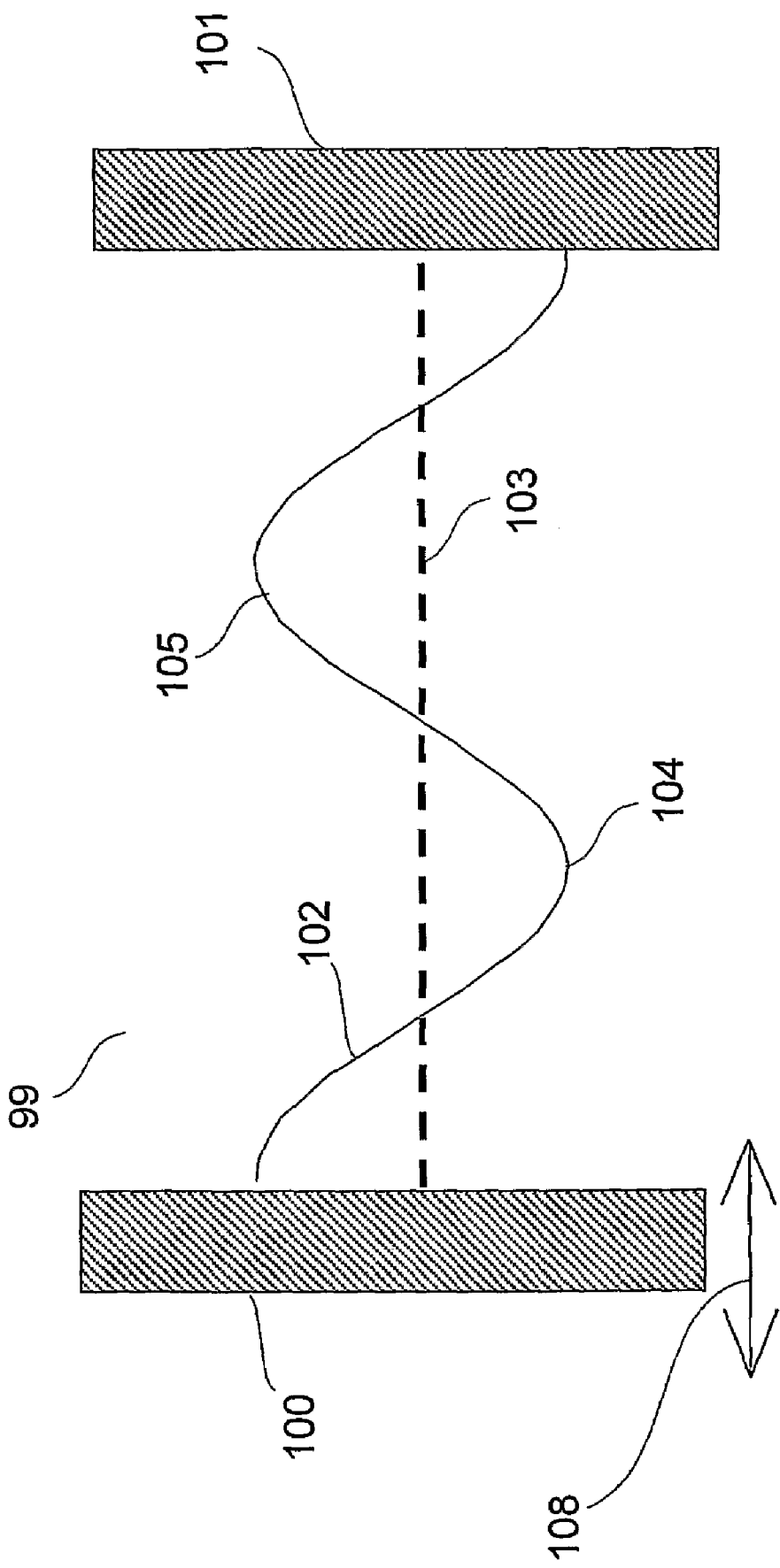
FIG. 3a is a schematic representation of an acoustic pressure wave between two electrodes.

FIGS. 3a and 3b and FIGS. 4a and 4b are used to illustrate the ion focusing properties of the electro-acoustic ion transmission device. In this non-limiting example the device operates without the asymmetric waveform of FAIMS and without the compensation voltage of FAIMS. An analyzer region 99 is located between conductive electrodes 100 and 101. The conductive electrodes are connected to not illustrated electrical power supplies that provide both dc and ac voltages to one or both plates. A not illustrated acoustic wave generator, such as for instance a mechanical oscillator, causes mechanical oscillation 108 of electrode 100. At the appropriate frequency of oscillation 108, which is a function of the spacing of the electrodes and the operational conditions of the gas between the electrodes, an acoustic pressure wave 102 is produced in the gas. The frequency is selected to form a standing wave between the electrodes. At a first point in time, shown in FIG. 3a, the wave has a pressure minimum at 104 and a pressure maximum at 105. At a later point in time shown in FIG. 3b, the wave appears to have been reflected across the dashed line 103, and the pressure minimum 104 in FIG. 3a is replaced by a pressure maximum 106 in FIG. 3b, and the pressure maximum 105 in FIG. 3a is replaced by a pressure minimum 107 in FIG. 3b. As is typical of standing acoustic waves, the nodes of zero change in pressure remain stationary relative to the surfaces of the electrodes 100 and 101 in FIG. 3a and FIG. 3b.

Figure 3B:
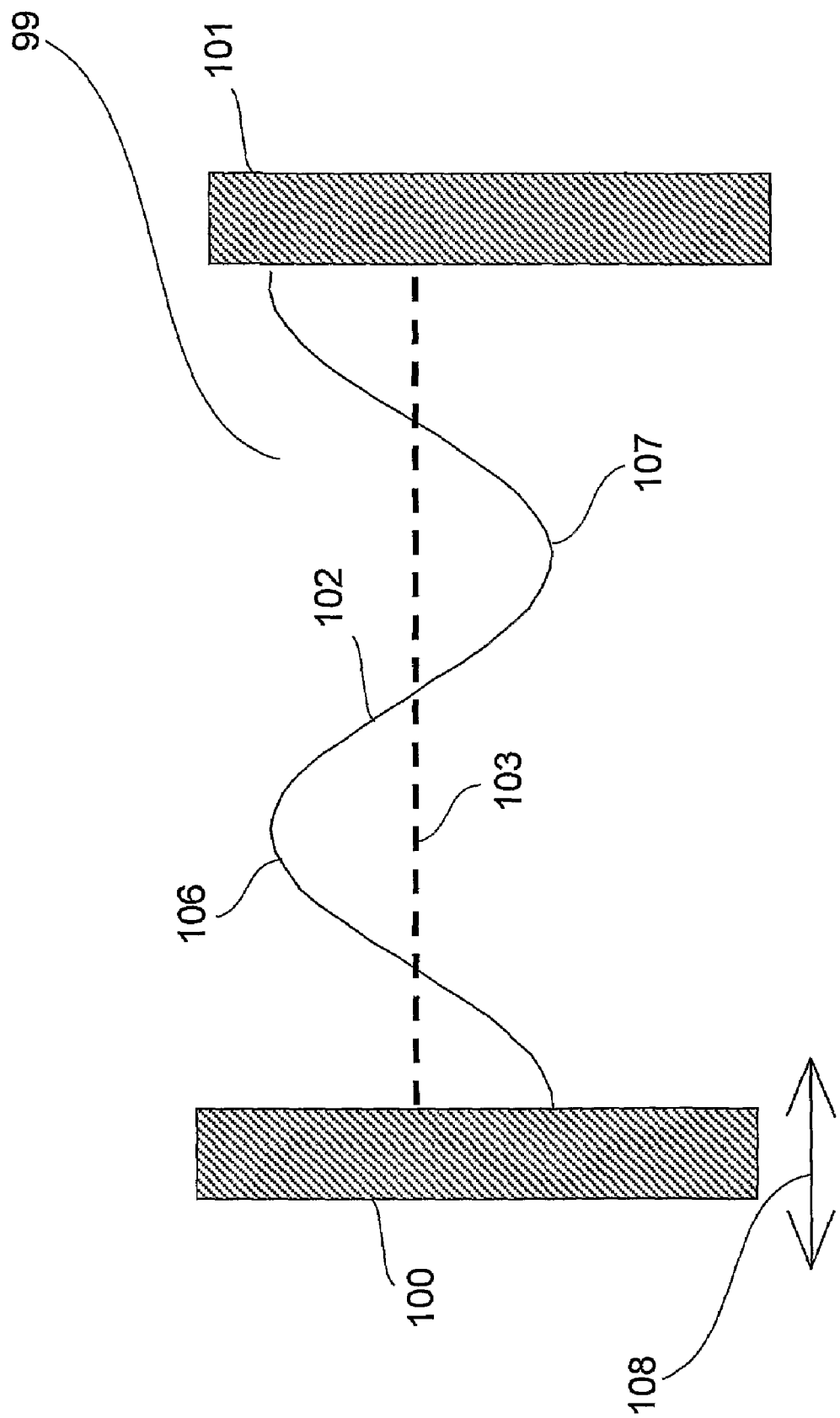
FIG. 3b is a schematic representation of an acoustic pressure wave between two electrodes.

FIGS. 4a and 4b closely resemble FIGS. 3a and 3b; however, an additional electric field 116 directed from right to left in FIG. 4a, and an electric field 117 directed from left to right in FIG. 4b have been generated by voltages applied to conductive electrodes 100 and 101. A positive voltage is applied to electrode 100 at a time corresponding to the location of the acoustic pressure wave shown in FIG. 4a, while a negative voltage is applied to electrode 100 at a time corresponding to the acoustic pressure wave shown in FIG. 4b. This is achieved through synchronization of the oscillatory motion 108 of electrode 100, and the applied voltages.

Still referring to FIGS. 4a and 4b, the unique ion focusing property of the electro-acoustic ion transmitter is illustrated by the motions of the ions 110, 111, 112 and 113. Under the conditions of the acoustic pressure wave 102 and applied electric field 116 shown in FIG. 4a, the ion 110 is located in a low pressure region indicated by the minimum 104 on the acoustic pressure wave 102. Similarly the ion 111 is located at a higher-pressure region indicated by the maximum 105 on the acoustic pressure wave 102. Adjacent to ion 110 is a right-pointing arrow having a length related to the ion velocity as it moves from left-to-right. Adjacent to ion 111 is a similar, but shorter arrow indicating a velocity in the same direction, but with a lower value. The ion located in a lower pressure region has a higher effective mobility in this region, and therefore travels more quickly than the ion 111, which is located in a region of higher pressure. This has the effect, when considering a cloud of ions in the region of ion 110 and ion 111, to move the ions in the vicinity of ion 110 so that they are approaching the ions that are located around ion 111. This means that the cloud of ions is being compressed as they move from left-to-right. The ions in the low-pressure region are moving faster than the ions in the high-pressure region. The acoustic pressure wave 102 has a sinusoidal form across the space between the electrodes 100 and 101, and therefore the velocities of ions at these individual locations are affected according to the pressure at that location. Nevertheless, it is clear that the sinusoidal pressure wave 102 has an extended portion of low pressure around pressure minimum 104, and an extended portion of higher pressure around pressure maximum 105.

At a next point in time, indicated by FIG. 4b, the pressure wave 102 has been reflected across the dashed line 103, and the low pressure and high pressure regions have alternated from their values in FIG. 4a. In FIG. 4b the polarity of the applied electric field 117 is reversed from that in FIG. 4a. This means that positively charged ions between plates 100 and 101 tend to travel from right-to-left in this figure. As noted in FIG. 4a, the ions do not all have the same velocity. Interestingly, and beneficially, the ion 112 is moving less rapidly than ion 113, because the ion 113 and the rest of the ions in the vicinity of ion 113 are in a lower pressure region of the acoustic wave 102. Again, as pointed out in FIG. 4a, the ions are being compressed, namely the ions following behind in the low pressure region 107 are traveling faster than those located in the high pressure region 106 shown on the acoustic wave 102 and therefore the ions in the low pressure region 107 are effectively catching up with the ions in the high pressure region. In both cases, FIG. 4a and FIG. 4b, the cloud of ions is being compressed as the ions in the rear of the flow are catching up with the ions at the front. As the conditions alternate between conditions at FIG. 4a and conditions at FIG. 4b, the cloud of ions tends to be compressed and focused towards the node 116 of the acoustic pressure wave 102. Those ions to the left of the dashed line 114 in FIG. 4a and to the right of dashed line 115 of FIG. 4b collide with the electrodes 100 and 101 respectively. If the acoustic wave 102 includes a plurality of repeating sinusoidal waves, there will be a plurality of focus points and the ions will accumulate in a series of bands between the electrodes.

Still referring to FIG. 4a and FIG. 4b. The focusing of the ions may be understood in a simple manner. Consider the ion 110 in FIG. 4a. Under the conditions shown in FIG. 4a this ion is moving to the right, with a velocity that is slightly enhanced because it is in a region of lower pressure. If conditions are changed to those in FIG. 4b, the ions in the same region namely ion 112 moves to the left with a slower velocity, because it is in a region of higher pressure. If the net distance traveled by the ion 110 and 112 through the entire cycle of pressure and electric field is calculated, the ion moves towards the right in FIG. 4a and FIG. 4b because the velocity in FIG. 4a exceeded that in the opposite direction in FIG. 4b. If the net distance traveled during each cycle is towards the right, the ion migrates towards the node 116. In other words, any ion that starts its motion between the node 116 and the dashed line 114 located at the next adjacent node, migrates to the right, and therefore migrates towards the node 116. By an analogous argument the ion represented by 111 and 113 in FIG. 4a and FIG. 4b migrates in the direction away from electrode 101. The ion velocity to the left in FIG. 4b of the ion 113 exceeds that of the ion velocity to the right of ion 111 in FIG. 4a. In other words all of the ions located between the node 116 and the right dashed line 115 at the next node to the right of node 116, migrate to the left in these figures. All of the ions between dashed line 114 and 115 migrate, over the course of many repeat cycles of the waveform, in a direction towards the node 116. This creates a focus region at note 116.

Figure 5:
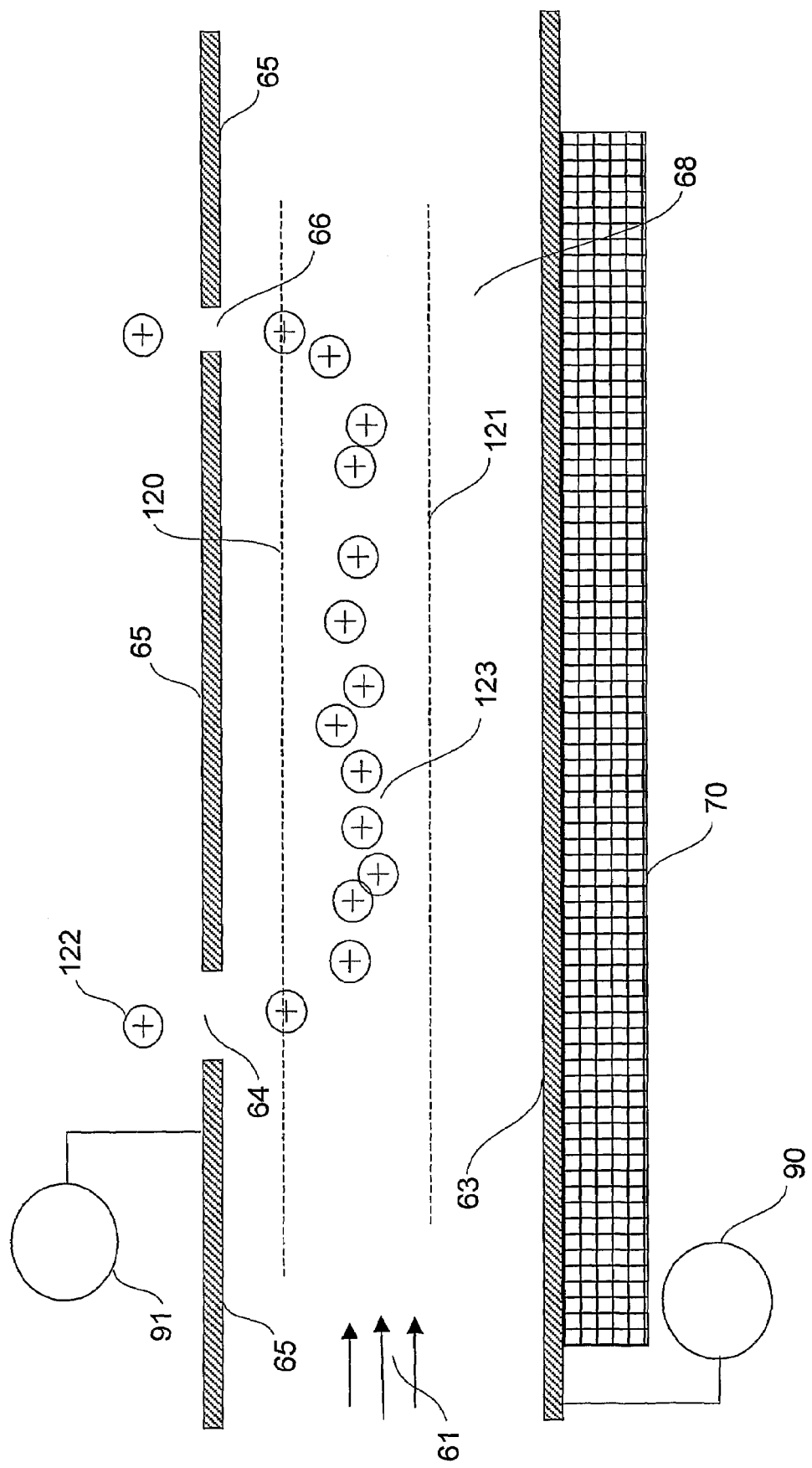
FIG. 5 illustrates the focused transmission of ions in a parallel plate version of the electro-acoustic ion transmission device.

FIG. 5 closely resembles FIG. 2 and includes an ion inlet 64 and an ion outlet 66, and a flow of gas 61 that transports the ions along the analyzer region 68. For simplicity of consideration of the ion transport in this figure it is assumed that the asymmetric waveform of FAIMS and the compensation voltage of FAIMS are not in operation. The ions 123 are focused between two nodes 120 and 121, which are not necessarily drawn in their exact expected locations, of the acoustic waveform that is generated by oscillation of the mechanical transducer 70. From FIG. 4a and FIG. 4b, it is apparent that the nodes 120 and 121 are separated by one complete cycle of the acoustic pressure wave. That is to say there is one additional, not illustrated node between the nodes 120 and 121 in FIG. 5.

Still referring to FIG. 5, the voltage difference between the upper electrode 65 and the lower electrode 63 is oscillated in synchronization with the oscillation of the acoustic pressure wave in the manner described in FIGS. 3a and 3b and FIGS. 4a and 4b. The voltage difference optionally is alternated in sinusoidal or square wave fashion, as some non-limiting examples. The ions are carried into, and out of, the focusing region by the flows of gas inward through ion inlet 64 and outward through ion outlet 66. The focusing region does not cause all of the ions to accumulate in a zero-width band because of the dispersing effects of diffusion and electrostatic coulombic repulsion among the ions in the cloud. The resulting ion cloud occupies a region between the nodes 120 and 121. The loss of ions during transit through the analyzer region 68 is minimized if the cloud remains entirely between the nodes 120 and 121. If the cloud extends beyond nodes 120 and 121, a leakage of ions occurs and some of the ions are lost by collision with the electrodes.

Figure 6:
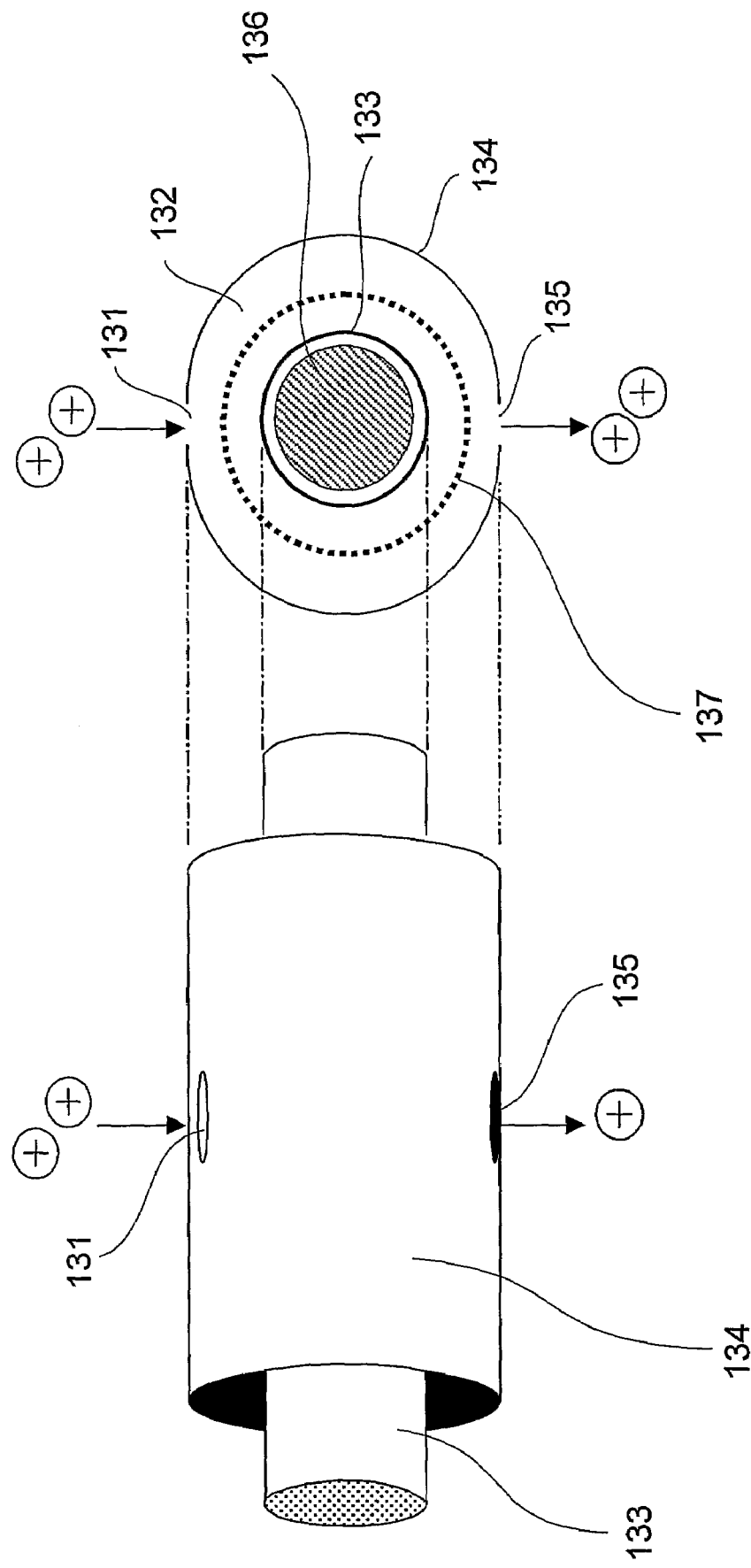
FIG. 6 is a cylindrical geometry electrode, suitable for both FAIMS and electro-acoustic ion transmission modes of operation.

FIG. 6 illustrates a cylindrical device that is operated optionally in FAIMS mode or in electro-acoustic ion transmission mode. Ions pass into an ion origin end of an annular analyzer space 132 between an inner electrode 133 and an outer electrode 134 via ion inlet 131. Ions that are transmitted through to an ion exit end of the analyzer region 132 exit the device via ion outlet 135. In FIG. 6, the inlet 131 and the outlet 135 are located at the same longitudinal location along the electrodes; however, in an optional version of these electrodes the ion inlet 131 is displaced some distance along the outer electrode 134 relative to the ion outlet 135. This optional arrangement provides additional transit time for the ions in the analyzer region 132, which may be beneficial for selecting a required subset of ions from a complex mixture.

Still referring to FIG. 6, inner electrode 133 comprises a transducer 136 that is actuated electrically to produce acoustic waves in the radial direction between the inner electrode 133 and the outer electrode 134. At an appropriate frequency, for given dimensions of the device and operating conditions of gas pressure, temperature etc., a standing acoustic pressure wave is formed between the inner electrode 133 and the outer electrode 134. When combined with a synchronized varying voltage difference applied between the inner electrode 133 and the outer electrode 134, the ions are focused into one or more bands between the electrodes, thereby improving the efficiency of ion transmission between the ion inlet 131 and the ion outlet 135. In FIG. 6, a focus region 137 is located in the annular region between the inner electrode 133 and the outer electrode 134. Although a single dashed line is used to represent the focus region 137 in FIG. 6, it is to be understood that this line represents the imaginary line towards which ions on either side migrate over several cycles of the acoustic wave and the applied synchronized electric voltage. In practice, the ions are distributed over a range of radial distance on both sides of the focus region 137.

Figure 7:
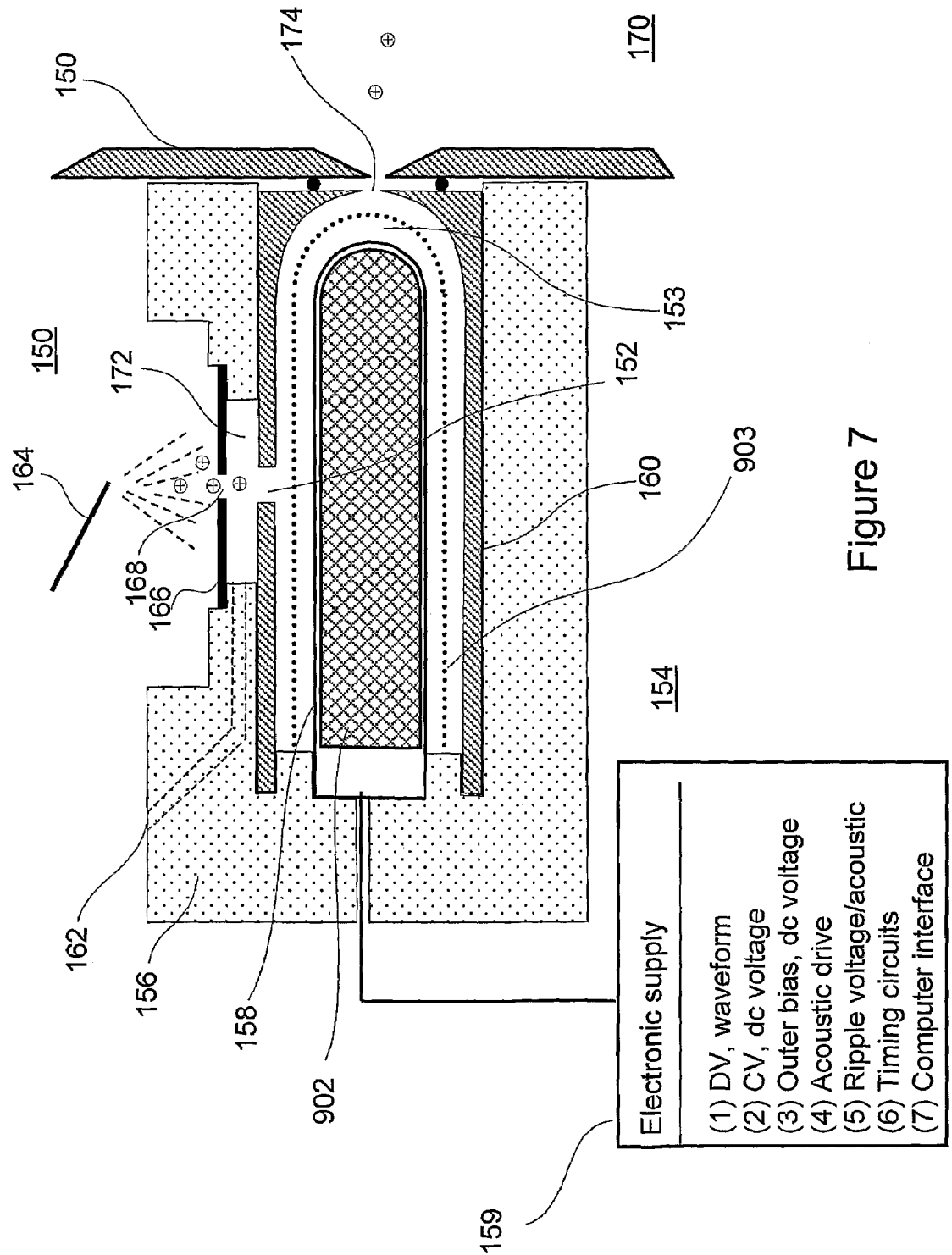
FIG. 7 is a cylindrical geometry electrode with a domed inner electrode, suitable for both FAIMS and electro-acoustic ion transmission modes of operation.

Referring now to FIG. 7, shown is a longitudinal cross-sectional view of an electrospray ion source 150 disposed in fluid communication with an ion inlet 152 of a FAIMS 154, the FAIMS 154 being mounted in and supported by an insulating material 156. As shown in FIG. 7, the inner electrode 158 and the outer electrode 160 are supported in a spaced-apart arrangement by an insulating material 156 with high dielectric strength to prevent electrical discharge. Some non-limiting examples of suitable materials for use as the insulating material 156 include Teflon®, and PEEK. A passageway 162 for introducing a curtain gas is shown by dashed lines in FIG. 7. An optional transducer 902 provides a mechanical oscillation to the surface of the inner electrode 158, to form acoustic pressure waves between the inner electrode 158 and the outer electrode 160. When the device is operated in electro-acoustic transmission mode, for example to provide a mode wherein the FAIMS separation mode is deactivated, but wherein the ion transmission remains high, one or more ion focusing regions 903 surround the inner electrode 158, and assist in transmitting ions between the ion inlet 152 and the ion outlet 174.

In FIG. 7, the ions are formed near the tip of an electrospray needle 164 and drift towards a curtain plate 166. The curtain gas, which is introduced below the curtain plate 166 via the passageway 162, divides into two flows, one of which exits through an aperture 168 in the curtain plate 166, to prevent neutrals and droplets from entering the curtain plate aperture 168. Ions are driven against this flow of gas by a voltage gradient between the needle 164 and the curtain plate 166. A field generated in the desolvation region 172 between the curtain plate 166 and the FAIMS outer electrode 160 pushes ions that pass through the aperture 168 in the curtain plate 166 towards the ion inlet 152 of FAIMS 154. A portion of the curtain gas flows into the ion inlet 152 and carries the ions along the length of the FAIMS electrodes to an ion exit 174, and into a mass spectrometer 170.

Still referring to FIG. 7, in a FAIMS mode of operation a high voltage asymmetric waveform is generated by supply 159 and is applied to the inner electrode 158 of FAIMS 154 via a not illustrated electrical contact, and a compensation voltage is generated by supply 159 and applied to the inner electrode 158, to select a subset of ions for transmission through FAIMS. In a second optional mode of operation the asymmetric waveform is removed, and the compensation voltage is removed. The acoustic transducer is activated by a not-shown power supply to form an acoustic pressure wave across the space between the inner electrode 158 and the outer electrode 160. Optionally the transducer is located outside of the outer electrode 160. Further optionally the surface of the transducer is coated with electrical conductive layer serving as the surface of one of the electrodes. Further optionally, transducers are coupled to both the inner electrode 158 and to the outer electrode 160. Further optionally, the actuation of these two transducers is synchronized. Further optionally, the gas in the region between the inner electrode 158 and the outer electrode 160 is set into acoustic oscillation by a means other than a simple mechanical transducer, including via coupling through openings along one or both of the inner electrode 158 and outer electrode 160.

Still referring to FIG. 7, an ac sinusoidal voltage is generated by supply 159, and applied to the inner electrode 158 with a frequency that matches that of the acoustic wave, to form an ion focusing region 903 that helps to enhance the transmission efficiency of the device and to minimize loss of ions that are being transmitted from the ion inlet to the ion outlet. The ions that approach the ion outlet optionally are focused sufficiently strongly to produce a trapping region, or a near-trapping region, near the hemispherical tip of the inner electrode 158.

Figure 8:
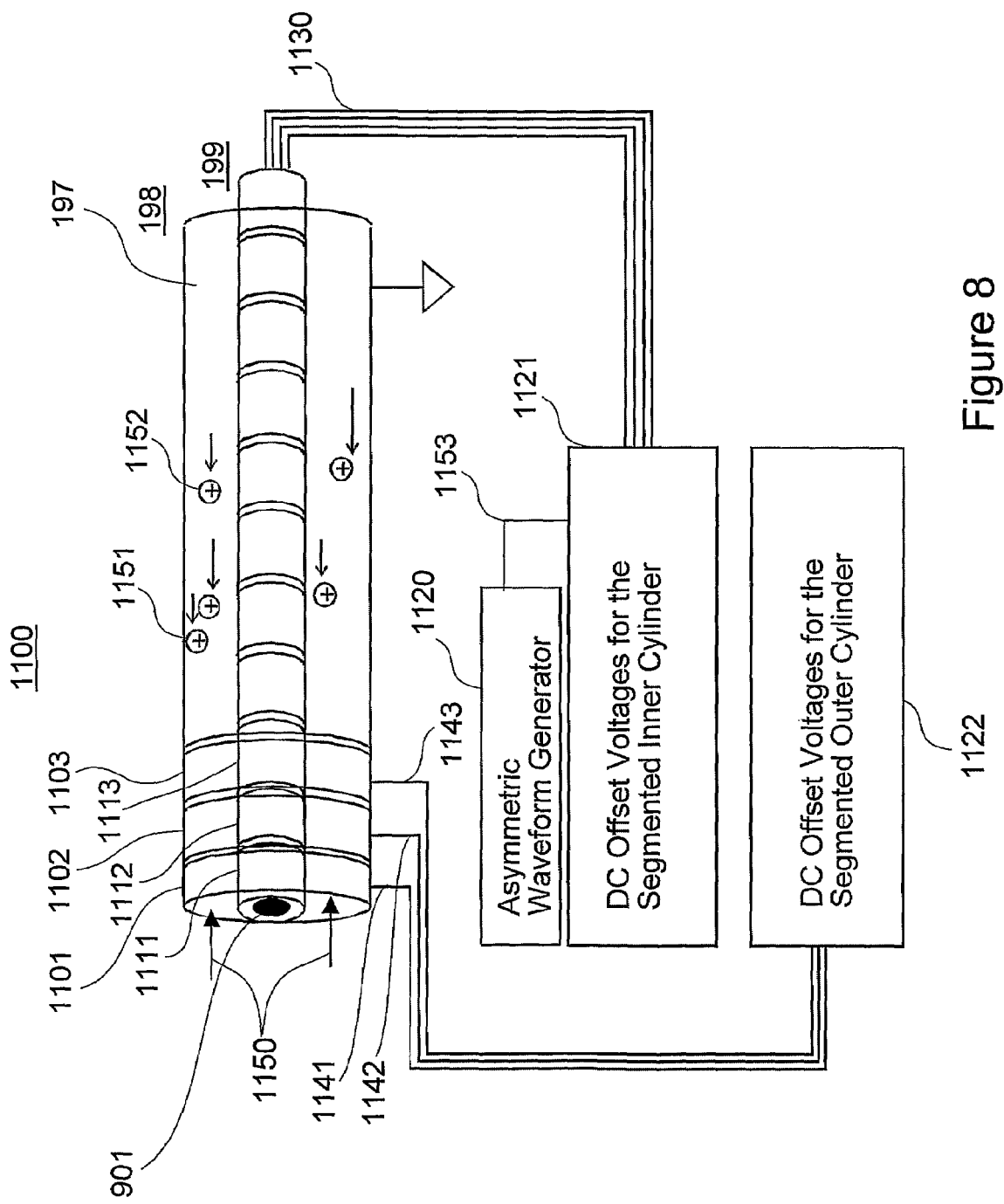
FIG. 8 is a segmented cylindrical electrode suitable for both FAIMS and electro-acoustic ion transmission modes, which may be combined with longitudinal fields generated by voltages applied to the segments.

Referring now to FIG. 8, shown is a simplified view of a cylindrical segmented FAIMS 1100. The segmented inner electrode 199 includes a series of segments 1111, 1112, 1113 as well as further segments not enumerated, and the outer segmented electrode 198 is similarly subdivided into segments 1101, 1102, 1103 and further segments not enumerated. The inner segmented electrode 199 and the outer segmented electrode 198 are spaced apart by not-shown insulating support members. The segments comprising the segmented inner electrode 199 are electrically isolated from each other to permit application of independent voltages to each segment. Preferably the segments are close together, so maintaining high voltage differences between the adjacent segments is expected to cause electrical discharges between the segments. Preferably therefore, voltage differences between adjacent segments are low enough to avoid electrical discharge.

Still referring to FIG. 8, the segments comprising the segmented inner electrode 199 and the segmented outer electrode 198 are spaced apart from each other by not-shown insulators. Preferably, the segments are closely spaced and the insulators separating the segments are not 'visible' to the ion flow. The collision of an ion with an insulating material produces an electric charge on the insulating material, because by definition the insulator cannot carry away the electricity. The electric charge is not controlled, and produces unpredictable electrostatic fields around the charged insulating surface. This means that preferably the not-shown insulator between segments 1111 and 1112 etc. is recessed below the outer surfaces of the segments 1111, 1112, 1113 and other segments that comprise the annular analyzer region 197. It is preferable that the ions 1151, 1152 and other ions that are flowing along the annular analyzer region 197 avoid collision with the not-shown insulation material that separates segments 1111 and 1112 etc. one from another. In this example the not-shown insulating material separating each pair of segments comprising both segmented inner electrode 199 and outer segmented electrode 198 is sufficiently below the surfaces of the segments that face into the analyzer region 197, such that the electrostatic charge build up on the surfaces of the insulating material because of collisions with ions has minimum affect on the overall electric fields in the analyzer region 197.

Still referring to FIG. 8, a flow of gas 1150, shown as solid headed arrows, flows in the annular region 197 between the segmented inner and outer electrodes 199 and 198 respectively. A not-shown ion source provides ions to the annular region 197, where the ions are caused to move by electric fields generated by application of voltages to the segments comprising the inner and outer segmented-electrodes. In the example shown in FIG. 8 the ions 1151, 1152 and other ions not enumerated are transported by electric fields in a direction contrary to the flow of gas 1150. The voltages applied to consecutive segments is selected in this example to produce an electric field gradient that causes ions 1151, 1152 and other ions to be moved in the direction shown by the open headed arrows, while the gas 1150 flows in a direction shown by the closed headed arrows. Voltages are applied to the segments by electric power supplies 1120, 1121 and 1122. Connections to every segment of the inner segmented electrode 199 and outer segmented electrode 198, including electrical contacts on the electrode segments, are not shown. The bundle of connections 1130 provides voltages from power supply 1121 to the segments 1111, 1112, 1113 and the other segments of the inner segmented-electrode 199. In this example the voltage applied consists of a radio-frequency (rf) ac component added to a dc voltage, where the rf component is equal in every segment, but the dc voltage optionally differs amongst the segments of the inner segmented electrode 199. Similarly a bundle of connectors 1141, 1142, 1143 and others not shown, provide voltages from outer bias power supply 1122 to the segments 1101, 1102, 1103 and others not shown of the outer segmented-electrode 198. In this example, the voltages applied to the outer segmented-electrode 198 differ amongst the segments, and in this case rf voltage is not applied to any parts of the outer segmented electrode 198.

Still referring to FIG. 8, the rf voltage applied to the inner segmented electrode 199 is an asymmetric waveform produced by waveform generator voltage supply 1120 and delivered to power supply 1121 through connector 1153. The power supply 1121 provides a dc voltage offset, superimposed on the asymmetric waveform, to each segment of the segmented inner electrode 199, routed to an electrical contact of each segment by an independent conductor comprising the bundle of connections 1130.

Still referring to FIG. 8, the series of segments are used to propel the ions along the length of the device, in a way that optionally is independent of the flow of gas. Application of an appropriate waveform to the series of segments results in capture of the ions among certain segments, or forms a series of traveling waves. Advantageously, operation of the device in FAIMS mode and in electro-acoustic mode optionally is superimposed upon the operation of the segments. For example, a transducer 901 optionally is located as part of the inner electrode, or further optionally in mechanical communication with the outer electrode to produce an acoustic pressure wave within the annular space between the inner electrode 198 and the outer electrode 199. A selected oscillating voltage difference between the outer segment 1101 and 1111 is applied to be in synchronization with the acoustic pressure wave. This oscillating voltage is superimposed on the dc level that is common to both segment 1101 and 1111. Similarly, the selected oscillating voltage difference is applied between segments 1102 and 1112, again superimposed on the dc level of that pair of segments. This continues throughout the segments of the device.

Still referring to FIG. 8, the cloud of ions is constrained within certain radial locations by the electro-acoustic ion transmission mode, but simultaneously forced to move along the length of the device by control of the dc voltage offsets applied to the individual segment pairs, for example the pair of segments 1101 and 1111, and the pair of segments 1102 and 1112, and so on throughout the device. In a non-limiting example the dc level of segments 1101 and 1111 is 10 volts, and the dc level of segments 1102 and 1112 is 9 volts, and the dc level of segments 1103 and 1113 is 8 volts, and so on through the electrodes. For example a sinusoidal voltage is applied to the inner electrodes to produce a 10 volt p-p superimposed on the dc level of each inner electrode. Continuing this example, the dc level of inner electrode 1111 is 10 volts, plus a sinusoidal wave that carries the voltage 5 volts more positive (up to +15 V) and 5 volts more negative (down to +5 V) than the dc value of 10 volts. Similarly, the dc level of inner electrode 1112 is 9 volts, now with an added a sinusoidal wave that carries the voltage 5 volts more positive (to +14 V) and 5 volts more negative (i.e. to +4 V) than the dc value of 9 volts. Under these dc levels amongst the segments, a positive ion is caused to drift from right to left in FIG. 8. In this non-limiting example the series of segments are arranged to produce a uniform longitudinal drift along the annular tube. If a pulse of ions is introduced at the inlet, the ions are separated in the manner of conventional drift tube ion mobility spectrometry, namely the highest mobility ions traversing the device more quickly than the lowest mobility ions. This device, because of the added benefit of the electro-acoustic ion focusing has very good ion transmission efficiency.

Figure 9:
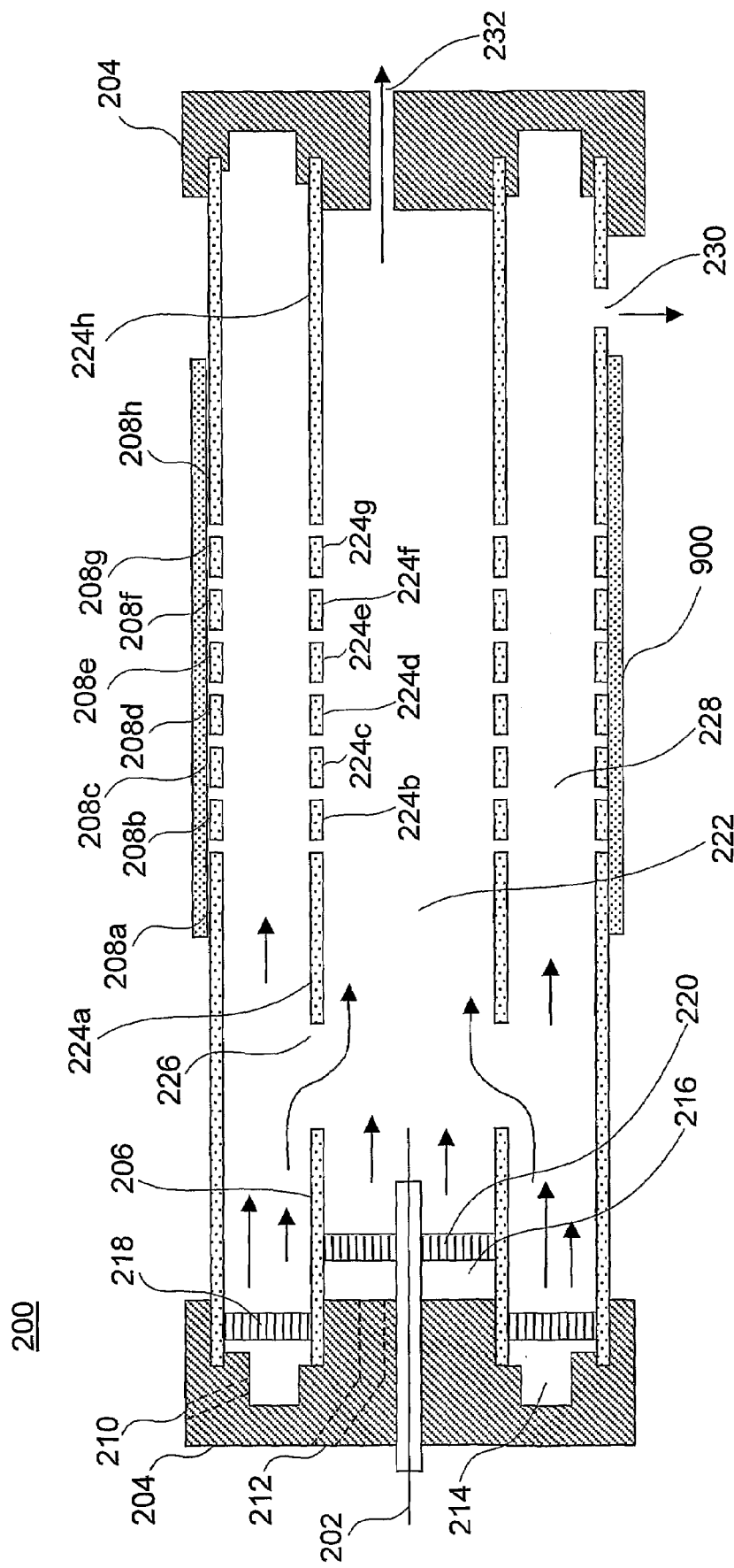
FIG. 9 is a segmented electrode with internal ionization, suitable for both FAIMS and electro-acoustic ion transmission modes, either or both of which can be combined with longitudinal fields generated by voltages applied to the segments.

FIG. 9 is a cylindrical geometry FAIMS 200, with a segmented inner electrode 224 comprised of segments 224a to 224h and outer electrode 208 comprised of segments 208a to 208h. Short segments 224b to 224g are spaced apart from similar length segments 208b to 208g. Ions are produced by ionizer 202 which may include electrospray ionization, corona discharge, and atmospheric pressure chemical ionization as some non-limiting examples. The ionizer 202 is mounted at an ion origin end in an insulating member 204, which also serves to support a short inner cylinder 206 and a long outer cylinder 208. A flow of carrier gas passes through a passageway 210 shown by dashed lines in insulating member 204, and a flow of sampler gas flows through passageway 212 shown by dashed lines in insulating member 204. The carrier gas enters a pressure equalization chamber 214, and the sampler gas enters a second equalization chamber 216. Diffusers 218 and 220 serve to restrict the carrier and sampler gases respectively and to allow these gases to flow uniformly around the circumference of the electrodes. The carrier gas passes through the diffuser 218, and flows in a smooth laminar flow along the annular space between the short inner cylinder 206 and the long outer cylinder 208. Similarly the sampler gas passes through the diffuser 220, and flows in a smooth laminar flow along the annular space between the ionizer 202 and the short inner cylinder 206. The sampler gas flows through the inner passage 222 within the inner electrode 224.

Still referring to FIG. 9, the ions that are produced by ionization source 202 are accelerated away from the source 202 in an outwardly radial direction by a voltage difference between the ionization source 202 and the short inner cylinder 206. Some ions pass through a gap 226 between the short inner cylinder 206 and the first segment of the inner cylinder 224a. Those ions that pass through the gap 226 are entrained by the carrier gas and carried along the analyzer region 228, which is the annular space between the inner cylinder 224 and the long outer cylinder 208. The ions for which the applied waveform voltage and the compensation voltage are appropriate, pass through the analyzer region 228, and are carried by the carrier gas to an ion exit end of the analyzer region 228 and out of the FAIMS 200 via ion outlet 230. Optionally, the ions are further analyzed by mass spectrometry, or other types of ion mobility spectrometers, or further FAIMS devices, or are detected using ion detection technologies including amperometric or photometric as some non-limiting examples.

Still referring to FIG. 9, optionally an asymmetric waveform and compensation voltage are applied to the inner electrode 224 via a not illustrated electrical contact. Bias voltages are applied to the short inner electrode 206 and the long outer electrode 208. The segments that comprise the inner electrode 224 and the long outer electrode 208 optionally are at the same potential, or are at potentials that permit measurement of the low-field mobility of the ions that are successfully transmitted at the asymmetric waveform voltage and the compensation voltage under the ambient conditions of gas composition, gas pressure, and gas temperature.

Still referring to FIG. 9, optionally a portion of the carrier gas that flows into the passageway 210 and through diffuser 218 enters the inner passage 222 within the inner electrode 224 by flowing radially inward through the gap 226. This inward flow of carrier gas helps to desolvate ions from ionization source 202 that are flowing outward through gap 226. This countercurrent of flowing gas helps to desolvate the ions and also prevents neutrals coming from the ionization source from entering the analyzer region 228. The neutrals produced from the sample, but not ionized by the ionizer 202 flow with the sampler gas along the inner passage 222 within the inner electrode 224 and out of sample outlet port 232. Preferably a not illustrated gas pump assists in pulling the sampler gas out of port 232, and assists in pulling a desolvating portion of carrier gas inward radially through the gap 226.

Still referring to FIG. 9, the number of segments of the inner electrode 224 and of the outer electrode 208 optionally is larger or fewer than shown in this figure. Further discussions assume that the electrodes are divided into a large number of segments. The cylindrical arrangement of the inner and outer coaxially arranged electrodes shown in FIGS. 8 and 9 give rise to an ion focusing in the annular analyzer region between the inner and outer electrodes, for an ion transmitted at the selected asymmetric waveform (DV) and the selected compensation voltage (CV). This focusing helps to prevent ions from colliding with the inner and outer electrodes. The application of differing bias voltages on the segments of the segmented FAIMS shown in FIGS. 8 and 9 makes it possible to evaluate the low-field mobility of these ions, in an experiment conducted within the apparatus of the type shown in FIG. 9. Ions are therefore selected on the basis of their high-field mobility behavior to pass FAIMS at the selected DV and CV, as well as by their low-field mobility as selected by appropriate voltages and arrangements of voltages applied to the segments of the inner and outer electrodes.

Still referring to FIG. 9, the same drift tube ion mobility experiment optionally is conducted while the ions are focused using the electro-acoustic transmission mode. A transducer 900 is activated to produce acoustic pressure waves in the region between the outer electrode 208 and the inner electrode 224. Optionally the acoustic pressure waves are generated using other means, including coupling through the gaps between electrodes 208a, 208b etc. Further optionally the acoustic pressure waves are generated via mechanical coupling to the inner electrode 224. An ac voltage difference is applied between the inner electrode 224 and the outer electrode 208, superimposed on the dc potentials of the individual segments that make up these electrodes. As noted above, this means that the ions are focused and transmitted between the ion inlet with high efficiency, and are simultaneously subjected to one or more of a plurality of possible separations and measurements as a result of application of appropriate potentials to the segments that comprise the inner electrode 224 and the outer electrode 208. Optionally, application of potentials to the segments that comprise the inner electrode 224 and the outer electrode 208 is performed under computer control.

Figure 10:
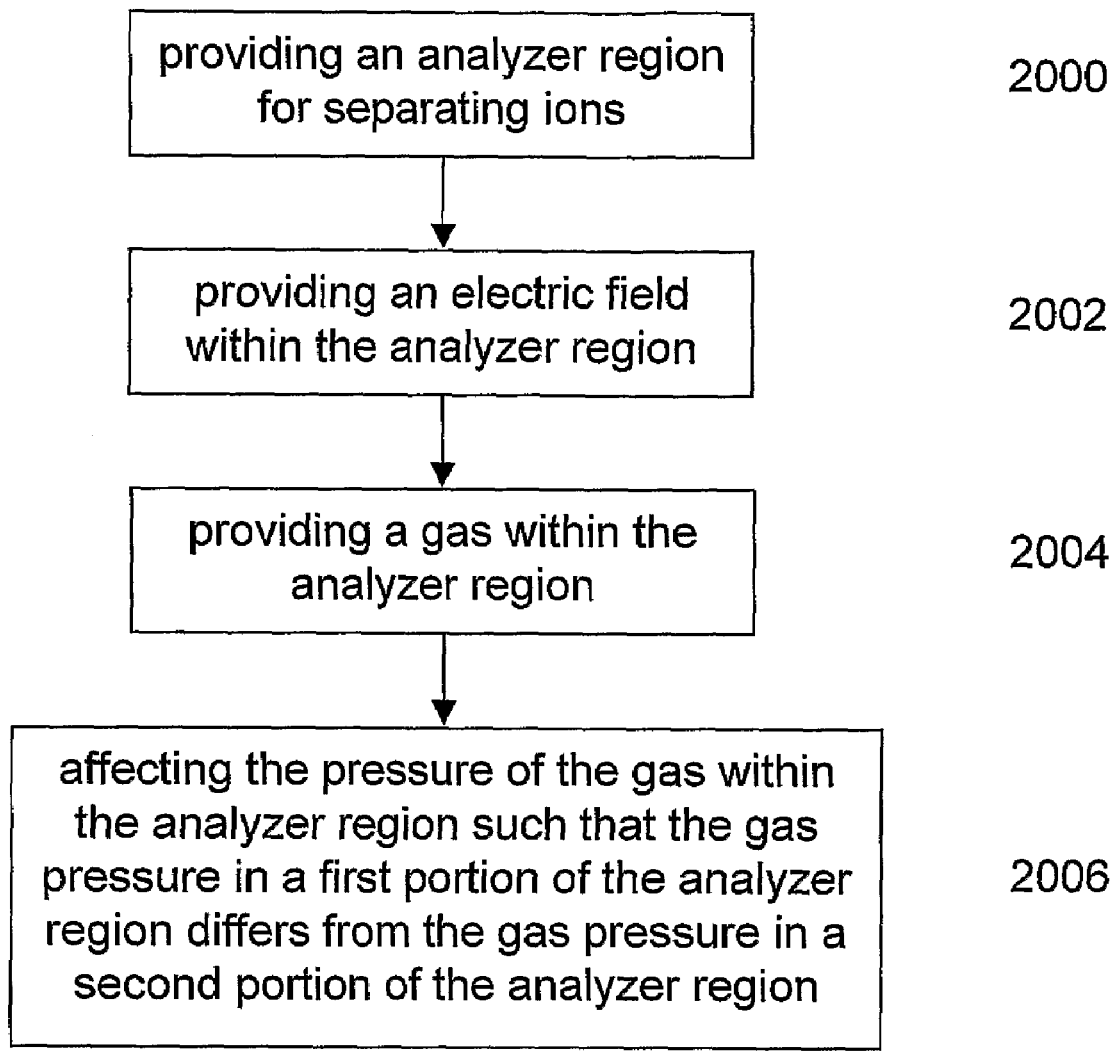
FIG. 10 is a simplified flow diagram of a method for separating ions according to an embodiment of the instant invention; and, FIG. 11 is a simplified flow diagram of another method for separating ions according to an embodiment of the instant invention.

Referring now to FIG. 10, shown is a simplified flow diagram of a method for separating ions according to an embodiment of the instant invention. At step 2000 an analyzer region is provided for separating ions. The analyzer region is defined by a space between a first electrode surface and a second electrode surface, the first electrode surface disposed in a spaced-apart facing relationship with the second electrode surface, the analyzer region in fluid communication with an ionization source and with an ion detecting device. At step 2002, an electric field is provided within the analyzer region by the application of a potential difference between the first electrode surface and the second electrode surface. The electric field is for affecting trajectories of ions along a direction normal to the first electrode surface and the second electrode surface. At step 2004 a gas is provided within the analyzer region. At step 2006 the pressure of the gas within the analyzer region is affected, such that the gas pressure in a first portion of the analyzer region differs from the gas pressure in a second portion of the analyzer region.

According to the method of FIG. 10, affecting the pressure of the gas within the analyzer region includes providing an acoustic pressure wave within the analyzer region. Optionally, the acoustic pressure wave is a standing acoustic pressure wave. An acoustic pressure wave is provided, for instance, by inducing an oscillatory motion of the first electrode surface relative to the second electrode surface, the oscillatory motion being oriented along a direction that is normal to at least one of the first electrode surface and the second electrode surface. In this way, the gas pressure in the first portion of the analyzer region and the gas pressure in the second portion of the analyzer region varies with time.

Figure 11:
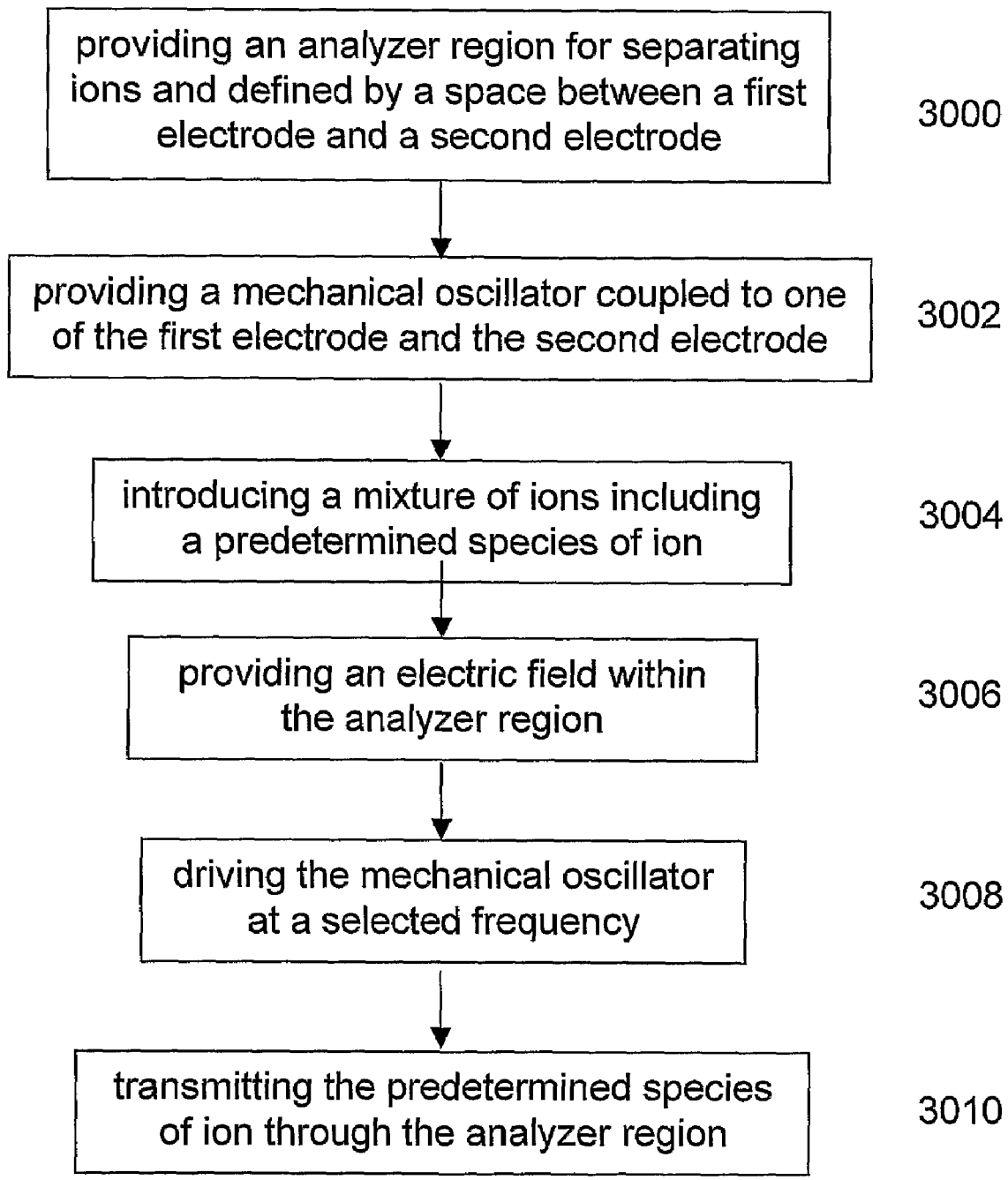

Referring now to FIG. 11, shown is a simplified flow diagram of another method for separating ions according to an embodiment of the instant invention. At step 3000 an analyzer region is provided for separating ions. The analyzer region is defined by a space between a first electrode and a second electrode, the first electrode comprising a first electrode surface and the second electrode comprising a second electrode surface, the first electrode surface disposed in a spaced-apart facing relationship with the second electrode surface. In particular, the analyzer region in fluid communication with an ionization source and with an ion detecting device. At step 3002 a mechanical oscillator is provided, coupled to one of the first electrode and the second electrode. At step 3004 a mixture of ions including a predetermined species of ion is introduced from the ionization source into the analyzer region. At step 3006 an electric field is provided within the analyzer region by the application of a potential difference between the first electrode surface and the second electrode surface. At step 3008, the mechanical oscillator is driven at a selected frequency for inducing a motion in the one of the first electrode and the second electrode, the selected frequency for supporting formation of an acoustic pressure wave within the analyzer region. At step 3010 the predetermined species of ion is transmitted through the analyzer region to the ion detecting device.

Numerous other embodiments may be envisaged without departing from the spirit and scope of the invention.

What is claimed is:

1. An apparatus for separating ions, comprising:
a first electrode and a second electrode disposed one relative to the other in a spaced-apart facing arrangement for defining an analyzer region therebetween, the analyzer region including an ion origin end and an ion exit end and having a length extending between the ion origin end and the ion exit end;
an electrical contact on one of the first electrode and the second electrode for receiving an electrical signal from a power supply for providing a voltage difference across the analyzer region between the first electrode and the second electrode; and,
an acoustic pressure wave generator for providing an acoustic pressure wave within the analyzer region between the first electrode and the second electrode.

2. An apparatus according to claim 1, wherein the acoustic pressure wave generator comprises a mechanical oscillator in communication with one of the first electrode and the second electrode for imparting an oscillatory motion thereto.

3. An apparatus according to claim 1, wherein the acoustic pressure wave generator comprises a first mechanical oscillator in communication with the first electrode for imparting an oscillatory motion thereto and a second mechanical oscillator in communication with the second electrode for imparting an oscillatory motion thereto.

4. An apparatus according to claim 1, comprising a controller for synchronizing the providing of the voltage difference across the analyzer region and the providing of an acoustic pressure wave within the analyzer region, such that the voltage difference and the acoustic pressure wave co-operate to focus ions within the analyzer region.

5. An apparatus according to claim 1, wherein the first electrode comprises a plurality of first electrode segments, each first electrode segment spaced-apart from an adjacent first electrode segment of the plurality of first electrode segments along the length of the analyzer region.

6. An apparatus according to claim 5, wherein the second electrode comprises a plurality of second electrode segments, each second electrode segment spaced-apart from an adjacent second electrode segment of the plurality of second electrode segments along the length of the analyzer region, and each second electrode segment spaced-apart from a facing first electrode segment of the plurality of first electrode segments so as to define a plurality of spaced-apart electrode segment pairs.

7. An apparatus according to claim 1, wherein the first electrode and the second electrode each comprise a flat plate electrode disposed in a parallel facing relationship one relative to the other.

8. An apparatus according to claim 1, wherein the first electrode and the second electrode comprise inner and outer generally cylindrical electrode bodies, respectively, the first electrode comprising a curved outer surface and the second electrode comprising a curved inner surface, the curved outer surface overlapping a portion of the curved inner surface when in an assembled condition.

9. An apparatus according to claim 1, comprising an ion detecting device in fluid communication with the ion exit end of the analyzer region for detecting ions that are transmitted selectively through the analyzer region between the ion origin end and the ion exit end.

10. A method of separating ions, comprising:
providing an analyzer region for separating ions and defined by a space between a first electrode surface and a second electrode surface, the first electrode surface disposed in a spaced-apart facing relationship with the second electrode surface, the analyzer region in fluid communication with an ionization source and with an ion detecting device;
providing an electric field within the analyzer region by the application of a potential difference between the first electrode surface and the second electrode surface, the electric field for affecting trajectories of ions along a direction normal to the first electrode surface and the second electrode surface;
providing a gas within the analyzer region; and,
affecting the pressure of the gas within the analyzer region by providing an acoustic pressure wave within the analyzer region such that the gas pressure in a first portion of the analyzer region differs from the gas pressure in a second portion of the analyzer region.

11. A method according to claim 10, wherein the acoustic pressure wave is a standing acoustic pressure wave.

12. A method according to claim 10, wherein affecting the pressure of the gas within the analyzer region comprises inducing an oscillatory motion of the first electrode surface relative to the second electrode surface, the oscillatory motion oriented along a direction that is normal to at least one of the first electrode surface and the second electrode surface.

13. A method according to claim 12, wherein the induced oscillatory motion of the first electrode surface relative to the second electrode surface is for providing an acoustic pressure wave within the analyzer region.

14. A method according to claim 13, comprising selecting a frequency of the induced oscillatory motion of the first electrode surface relative to the second electrode surface in dependence upon a set of current operating conditions.

15. A method according to claim 14, wherein the selected frequency is for providing a standing acoustic pressure wave under the set of current operating conditions.

16. A method according to claim 10, wherein the gas pressure in the first portion of the analyzer region and the gas pressure in the second portion of the analyzer region varies with time.

17. A method according to claim 16, wherein the time-averaged gas pressure in the first portion of the analyzer region is the same as the time-averaged gas pressure in the second portion of the analyzer region.

18. A method according to claim 16, wherein the potential difference applied between the first electrode surface and the second electrode surface varies with time.

19. A method according to claim 10, wherein providing an electric field within the analyzer region comprises providing an asymmetric waveform voltage between the first electrode surface and the second electrode surface.

20. A method according to claim 19, comprising providing a direct current compensation voltage between the first electrode surface and the second electrode surface, the direct current compensation voltage being selected for transmitting a predetermined species of ion between the ion origin end of the analyzer region and the ion exit end of the analyzer region.

21. A method according to claim 10, wherein providing an electric field within the analyzer region comprises providing a sinusoidal ripple voltage between the first electrode surface and the second electrode surface.

* * * * *